(12) United States Patent
Shin (10) Patent No.: US 9,632,017 B2
(45) Date of Patent: Apr. 25, 2017

(54) METHOD AND APPARATUS FOR IMAGING CELLS

(71) Applicant: GWANGJU INSTITUTE OF SCIENCE AND TECHNOLOGY, Gwangju (KR)

(72) Inventor: Sang Mo Shin, Gwangju (KR)

(73) Assignee: Hanbat National University Industry Academic Cooperation Foundation, Daejeon (KR)

(*) Notice: Subject to any disclaimer, the term of this patent is extended or adjusted under 35 U.S.C. 154(b) by 77 days.

(21) Appl. No.: 14/412,918

(22) PCT Filed: Jul. 5, 2013

(86) PCT No.: PCT/KR2013/006011
§ 371 (c)(1),
(2) Date: Jan. 5, 2015

(87) PCT Pub. No.: WO2014/007585
PCT Pub. Date: Jan. 9, 2014

(65) Prior Publication Data
US 2015/0160114 A1    Jun. 11, 2015

(30) Foreign Application Priority Data
Jul. 5, 2012 (KR) .................. 10-2012-0073417

(51) Int. Cl.
*G01N 15/10* (2006.01)
*G01N 1/42* (2006.01)
(Continued)

(52) U.S. Cl.
CPC ............ *G01N 15/10* (2013.01); *G01N 1/286* (2013.01); *G01N 1/42* (2013.01); *G02B 21/0028* (2013.01);
(Continued)

(58) Field of Classification Search
CPC .. G01N 15/10; G01N 1/42; G01N 2015/1006; G02B 21/0028; G02B 21/367
See application file for complete search history.

(56) References Cited

U.S. PATENT DOCUMENTS 3,978,686 A * 9/1976 Lechner ............... G01N 1/06
62/51.1
4,967,825 A * 11/1990 Brown, Jr. ........... B22D 23/00
164/46

(Continued)

FOREIGN PATENT DOCUMENTS

EP          2 416 165 A1    2/2012
KR    10-2011-0079516 A    7/2011

OTHER PUBLICATIONS

Atomic force microscope (AFM) combined with the ultramicrotome: a novel device for the serial section tomography and AFM/TEM complementary structural analysis of biological and polymer samples Anton E. Efimov*, Alexander G: Tonevitsky†, Maria Dittrich‡& Nadezda B. Matsko§ *NT-MDT Co., Moscow, Russia Journal of Microscopy, vol. 226, Pt 3 Jun. 2007.*

(Continued)

*Primary Examiner* — Nicole Ippolito
*Assistant Examiner* — Sean Luck
(74) *Attorney, Agent, or Firm* — Rabin & Berdo, P.C.

(57) ABSTRACT

The present invention provides the method and apparatus to acquire three-dimensional images of cells. The present invention comprises (a) preparing the solid-state specimen containing (i) cells, (ii) viruses, (iii) the liquid containing the cells, or (iv) the liquid containing the viruses; (b) acquiring the surface information on the said solid-state specimen; (c) removing the surface of the said solid-state specimen and forming a new surface; and (d) acquiring the information on the new surface. According to the present invention, provided is the cell imaging method to acquire information to (Continued)

grasp practically the condition of the cell. Also, the present invention can provide information on the molecules and atoms consisting various biomolecules and organelles present in the cells. Furthermore, the present invention can provide the information on the interaction between the biomolecules present in the cells and the organic relationship among intracellular organelles.

11 Claims, 2 Drawing Sheets

(51) Int. Cl.
*G02B 21/00* (2006.01)
*G02B 21/36* (2006.01)
*G01N 1/28* (2006.01)
*G01Q 60/42* (2010.01)

(52) U.S. Cl.
CPC ... *G02B 21/367* (2013.01); *G01N 2015/1006* (2013.01); *G01Q 60/42* (2013.01)

(56) References Cited

U.S. PATENT DOCUMENTS

| | | | |
|---|---|---|---|
| 5,497,656 A | 3/1996 | Kado et al. | |
| 2004/0120862 A1* | 6/2004 | Lang | B82Y 35/00 422/536 |
| 2004/0140427 A1 | 7/2004 | Korchev et al. | |
| 2011/0011190 A1 | 1/2011 | Subramaniam | |
| 2011/0182494 A1 | 7/2011 | Sokolov et al. | |

OTHER PUBLICATIONS

Electron Microscopy after Rapid Freezing on Surface and Substitution Fixation ' a Metal A. Van Harreveld and Jane Crowell Kerckhoff LaboratoTies of the Biological Sciences, California Institute of Technology, Pasadena, California Jul. 1964.*

Jurgen A. W. Heymann et al., "Site-specific 3D imaging of cells and tissues with a dual beam microscope", Journal of Structural Biology, 2006, pp. 63-73, vol. 155.

John S. Fletcher et al., "TOF-SIMS 3D Biomolecular Imaging of Xenopus laevis Oocytes Using Buckminsterfullerene (C60) Primary Ions", Anal. Chem., 2007, pp. 2199-2206, vol. 79.

European Search Report dated Feb. 1, 2016.

Y. Kim et al., "AFM study of surface phenomena based on $C_{60}$ film growth", Applied Surface Science, 1998, pp. 602-609, vol. 130-132.

Kei Kobayashi et al., "Imaging of fullerene molecules on Si(111)-7X7 surface with NC-AFM". Applied Surface Science, 2000, pp. 228-232, vol. 157.

K. Hirahara et al., "One-Dimensional Metallofullerene Crystal Generated Inside Single-Walled Carbon Nanotubes", Physical Review Letters, Dec. 18, 2000, pp. 5384-5387, vol. 85, No. 25.

D. C. G. Klein et al., "Ordered stretching of single molecules of deoxyribose nucleic acid between microfabricated polystyrene lines", Applied Physics Letters, Apr. 16, 2001, pp. 2396-2398, vol. 78, No. 16.

Yu Huang et al., "Directed Assembly of One-Dimensional Nanostructures into Functional Networks", Science, Jan. 26, 2001, pp. 630-633, vol. 291.

Toshio Ando et al., "A high-speed atomic force microscope for studying biological macromolecules", PNAS, Oct. 23, 2001, pp. 12468-12472, vol. 98, No. 22.

Clemens Möllers et al., "Tapping-Mode Atomic Force Microscopy Produces Faithful High-Resolution Images of Protein Surfaces", Biophysical Journal, Aug. 1999, pp. 1150-1158, vol. 77.

Thundat T. et al., "Atomic force microscopy of DNA on mica and chemically modified mica", Scanning Microsc., Dec. 1992, pp. 911-918, vol. 6, No. 4.

Helen G. Hansma et al., "Atomic force microscopy of DNA in aqueous solutions", Nucleic Acids Research, 1993, pp. 505-512, vol. 21, No. 3.

Matthew N. Murray et al., "Atomic force microscopy of biochemically tagged DNA", Proc. Natl. Acad. Sci., May 1993, pp. 3811-3814, vol. 90.

Eun Young Kwon, "Study on the Mechanical Characteristics of Living Cells using Atomic Force Microscope", Dept. of Mech. Eng., The graduate school, Yonsei University, Dec. 2006, pp. 24-26 and 33-35.

* cited by examiner

METHOD AND APPARATUS FOR IMAGING CELLS

TECHNICAL FIELD

The present invention provides the method and apparatus of imaging cells. More specifically, the present invention provides the method and apparatus to acquire three-dimensional images of cells.

BACKGROUND ART

In the field of modern cell biology, microbiology, and especially molecular biology, it is an important research subject to find what molecules a cell and its organelles are made of, how and what the molecules are made in which organelles, where the molecules are transported to, how their molecular structures change, and how they are decomposed in a cell and its organelles. The movement and growth of cells are the essential factors governing the normal physiological process of cells. If the movement and growth of cells are restricted, negative results such as tumor formations are induced.

Meanwhile, it is important to know the three-dimensional distribution and change of the molecules or elements constituting a cell in order to understand the cellular structure and the functions of individual cellular organelles. A representative method to find the three-dimensional distribution of the molecules and organelles constituting a cell is a fluorescent imaging technique.

The fluorescent imaging technique allows one to acquire fluorescent images after attaching the specific molecules of interest with florescent markers or after genetically engineering the specific molecules to express fluorescence, and to confirm the three-dimensional distribution of specific molecules. As an exemplary apparatus with the fluorescent imaging technique applied is a confocal laser microscope. However, the fluorescent technique has shortcomings that cells are imaged while in an unnatural state or an artificially engineered state where genetically engineered fluorescence is expressed or foreign fluorescence materials are introduced into the cell. In addition, in order to be able to observe specific molecules via the fluorescent imaging technique, the concentration of the molecules in the cell should be higher than a certain threshold level. Even after cells are genetically engineered to express fluorescence or after the fluorescent markers are attached, the molecules with low concentrations cannot be imaged. Moreover, because the fluorescence image comes from the fluorescent markers, one cannot know for sure whether the markers are attached to the specific molecules of interest.

If the concentration of the specific molecule of interest is low, one can increase the concentrations using the methods such as to over-stimulate the cells to overexpress the molecules of interest or to amplify the molecules in the case of DNA and RNA molecules. There is a generally used method in that over-stimulated and processed cells and control group cells are cultured at the same time to increase the number of the cells, then the cells are separated, lysed (cell lysis), centrifuged, and certain molecules of interest in the cells are examined to see their increase or decrease using gel electrophoresis or mass spectroscopy. But these methods take a long time and need expensive reagents. Besides, it is difficult to continuously observe the cells because the cells are fixed and dead. Moreover, the amount of expression of the molecules of interest may differ because some molecules have to be over-stimulated in order to measure.

As the cell imaging methods beside the said optical method and the said biochemical method, there are other methods to research the structures of cells and their organelles and the molecules constituting the cells and the organelles such as scanning electron microscopy (SEM), transmission electron microscopy (TEM), and atomic force microscopy (AFM), and scanning tunneling microscopy (STM).

Scanning electron microscopy is used to observe specimens by detecting the secondary electrons or backscattered electrons that are the most probable among the various signals generated from specimens when an electron beam scans over the sample surface. However, as for the electron scanning microscopy, it is difficult to image molecules, and it has a shortcoming that specimens have to be coated with high atomic number metallic materials after freeze drying.

Transmission electron microscopy is used to observe samples by enlarging with electric lenses the parallel electron beam after passing through the samples. Molecules can be imaged by the transmission electron microscopy, but it has shortcomings that it takes a long time to image and analyze a specimen and that the specimen has to be frozen and cut into thin slices.

An atomic force microscope is a microscope in that a pyramid shaped probe contacts the surface of a sample and scans two dimensionally. As for the atomic force microscope, inorganic or metallic specimens can be imaged. However, there is a problem of rapidly degrading resolving power when imaging cells containing water with 75~80% of the volume and the cells immersed in a culturing media. Also, instead of the excellent resolving power, the imaging area is very small, and the reliability of the cell images may be low because the living cells may change their shapes voluntarily or due to the effect of the probe.

A scanning tunneling microscope, a kind of scanning probe microscope, analyzes the surface configurations of a sample utilizing tunneling currents. In the case of the scanning tunneling microscope imaging with atomic resolution is possible, but imaging is impossible for the cells containing a lot of moisture because a scanning tunneling microscope is operable in a high vacuum.

Throughout the present description, many published papers and patents are referenced, and their citations are presented. The cited papers and the disclosed content of the patents, inserted as the reference in the present description statement, explain more clearly the level of the technology and the content of the present invention in the technological area to which the present invention belongs.

DISCLOSURE

Technical Problem

The inventors of the present invention have endeavored diligently to solve the said problems of the prior art, and as a result developed a three-dimensional imaging method and an apparatus for cells, enabling practical imaging of the molecules and various organelles in cells. In addition, the inventors developed a cell imaging method and an apparatus using which imaging living cells is possible by preventing the artifacts from the physical and chemical stimuli to living cells.

Therefore, the purpose of the present invention is to provide a cell imaging method. The other purpose of the present invention is to provide a cell imaging apparatus.

The other purposes and advantages of the present invention are made clearer by the detailed description, claims and drawings of the present invention described below.

Technical Solution

An aspect of the present invention provides a cell imaging method comprising the following steps: acquiring a solid-state specimen containing (i) cells, (ii) viruses, (iii) the liquid containing the cells or (iv) the liquid containing the viruses; acquiring the surface information of the said solid-state specimen; removing the surface of the said solid-state specimen to form a new surface; and acquiring the surface information on the new surface of the said solid-state specimen.

The inventors of the present invention endeavored diligently to solve the said problems of the prior art, and as a result developed a three-dimensional imaging method and an apparatus for cells, enabling practical imaging of the molecules and various organelles in cells. In addition, the inventors developed a cell imaging method and an apparatus using which imaging living cells is possible by preventing the uncontrolled environmental factors on the cells.

The detailed explanation of the present invention by step by step is as follows.

(a) Preparing a Solid-State Specimen

According to an embodiment, a solid-state specimen of (i) cells, (ii) viruses, (iii) the liquid containing the cells or (iv) the liquid containing the viruses is prepared first.

The present invention can be applied to various kinds of cells and viruses, and the solid-state specimen is prepared using such various cells, viruses, and the liquid containing the cells and viruses.

The cells, whose imaging is possible by the present invention, include prokaryotic or eukaryotic cells.

The prokaryotic cells, whose imaging is possible by the present invention, include bacteria (or eubacteria) and archae-bacteria. The examples of the bacteria, whose imaging is possible by the present invention, include *Escherichia coli, Thermus theromophilics, Bacillus subtilis, Bacillus stearothermophilus, Salmonella typhimurium, Pseudomonas, Streptomyces, Staphylococcus, Lactobacillus, Lactococcus* and *Streptococcus* but are not limited. The examples of the arch-bacteria, whose imaging is possible by the present invention, include *Methanococcus jannaschii* (Mj), *Methanosarcina mazei* (Mm), *Methanobacterium thermoautotrophicum* (Mt), *Methanococcus maripaludis, Methanopyrus kandleri, Halobacterim, Archaeglobus fulgidus* (Af), *Pyrococcus horikoshii* (Ph), *Pryobaculum aerophilum, Pyrococcus abyssi, Sulfolobus solfataricus* (Ss), *Sulfolobus tokoadii, Aeuropyrum pemix* (Ap), *Thermoplasma acidophilum* and *Thermoplasma volcanium*, but are not limited.

The eukaryotic cells, whose imaging is possible by the present invention, include fungus cells, yeast, and plant cells (for example, monocotyledonous plant, dicotyledonous plant, and algae) and animal cells (for example, mammals, insects, reptiles, and birds) but are not limited.

According to an embodiment, the animal cells, whose imaging is possible by this invention, include humans, mice, rats, cattle, pigs, horses, sheep, rabbits, goats, birds, fishes, and insects.

According to an embodiment, the animal cells, whose imaging is possible by the present invention, include blood cells, immune cells, stem cells, somatic cells, germ cells, tumor cells, cancer cells, and normal cells.

The viruses, whose imaging is possible by the present invention, include animal virus, plant virus, and bacteriophage, and their examples include HBV (hepatitis B virus), HCV (hepatitis C virus), HAV (hepatitis A virus), HIV (human immunodeficiency virus), retrovirus, Sendai virus, myxovirus, coronavirus, encephalomyelitis virus, rotavirus, cytomegalovirus, measles virus, vaccinia virus, rabies virus, Epstein-Ban virus, rhinovirus, polio virus, and herpes virus, but are not limited.

The solid-state specimen can be prepared by freezing (i) cells, (ii) viruses, (iii) the liquid containing the cells, or (iv) the liquid containing the viruses.

A frozen specimen can be acquired by freezing the cells or the viruses themselves. According to this convention, a frozen specimen can also be acquired by freezing the liquid containing cells or viruses. The liquid containing the cells or the viruses includes the media used for culturing the cells or the viruses, but is not limited.

The freezing to acquire the frozen specimen can be carried out by the various freezing methods disclosed to the skilled persons in the art. For example, the said freezing method can be carried out in the temperature ranges −200 C~15 C, −180 C~20 C, −150 C~35 C, and −200 C~55 C.

For example, the said freezing can be done by impregnating the cells in a mixture of solid carbon dioxide and alcohol or in liquid nitrogen. The said mixture of solid carbon dioxide and alcohol or liquid nitrogen can be contained in a container. The said container above can be positioned directly in the freezer, and the said freezer can be set at a desired temperature (for example, −35 C). The said freezer can be a programmable freezer or a freezer whose freezing speed can be controlled. The said frozen specimen can be stored at the temperatures below the glass transition temperature (for example at −135 C).

The said freezing can be done by rapid freezing. The definition, "rapid freezing", in this description means that the liquid is cooled generally by rapidly passing the maximum ice crystallization region (for example, −5 C~−1 C, more than 80% of solidification) within the minimum time duration (for example, within 30~35 minutes) in order to make the size of ice crystals small or to have non-crystalline ice (or vitrified ice) formed.

According to an embodiment, the freezing to acquire a solid-state specimen is to freeze rapidly to form non-crystalline ice, and this is a vitrification method. Alternatively, while rapid freezing, a freezing protectant such as DMSO (dimethyl sulfoxide) may be used.

Because the solid-state specimen is solid, a suitable imaging instrument, for example AFM or STM can be used to image the specimen with atomic/molecular resolution. Because at ambient temperatures the non-crystalline ice melts, it is desirable to image the specimen at the temperatures below the melting point. In addition, when imaging at an ambient pressure and at low temperatures, because the moisture in the air can freeze on the surface of the part of the instrument maintained at low temperatures, it is desirable to image in a dehumidified ambient (for example, in dry nitrogen).

(b) Acquiring the Surface Information from a Solid-State Specimen

The information is acquired from the surface of a specimen that was prepared by solidifying the liquid containing the said cells. The acquisition of the surface information is described in detail below.

(c) Forming a New Surface by Removing the Surface of the Solid-State Specimen

After the information is collected from the surface of a solid-state specimen, the surface of the solid-state specimen (for example, frozen specimen) is removed, and a new surface is formed in order to get three-dimensional images of the solid-state specimen (for example, frozen specimen).

The surface of the solid-state specimen (for example, frozen specimen) can be removed by sublimating the surface ice.

The water in a life ambient (for example, cells, tissues, bodily fluid, and blood) occupies more than 80% of the volume, and the ice, more desirably, non-crystalline ice formed during the fabrication of the specimen (for example, frozen specimen) should be removed so that the potential damages from the removal should be minimized. To accomplish this goal in the present invention, the ice on the surface of the solid-state specimen (for example, frozen specimen) is removed, in an original way, by sublimating the ice.

The sublimation can be carried out at constant temperatures below the triple point by changing the pressure. Alternatively, the sublimation for removing the surface is carried out at constant pressures by changing the temperature below the triple point. The said temperature for sublimation, for example, may be changed using heaters or coolers, and the said pressure change may be done using vacuum pumps or cold traps. In the phase diagram of water, only solid ice and water vapor exist at temperatures and pressures below the triple point. The solid-state changes directly to the gas state without going through the liquid state if the temperature is raised while maintaining the pressure constant. The solid-state changes also directly to the gas state without going through the liquid state if the pressure is lowered while maintaining the temperature constant. In this manner, the surface of the solid-state specimen is removed, and a new surface, which is the target for acquiring the surface information, is formed by sublimating the surface ice of the solid-state specimen (for example, frozen specimen).

When the surface of the solid-state specimen is removed, the ice is removed by sublimation, but macromolecules with large molecular weights, cell membranes and organelles remain without being sublimated. Such remaining macromolecules can give three-dimensional images that are deeper than the images acquired before the surface removal. However, if the depth of the remaining macromolecules or cell organelles is deeper than the height of the scanning probe, it is beyond the limit of imaging. In this case, it is desirable to remove the macromolecules or the cell organelles that are finished with imaging and to continue the subsequent imaging.

The surface of the solid-state specimen may be removed using physical forces or beams. Especially, such physical forces or beams are used to remove the macromolecules or cell organelles on the cell membrane surface or inside the cell.

When the said physical forces are used, it is desirable to push or pull the probe of the SPM (scanning probe microscope).

The SPMs mounted with suitable probe tips in the present invention may be AFM (atomic force microscope), STM (scanning tunneling microscope), BEEM (ballistic electron emission microscope), CFM (chemical force microscope), C-AFM, (conductive atomic force microscope), EFM (electrostatic force microscopy), ESTM (electrochemical scanning tunneling microscope), FMM (force modulation microscope), KPFM (kelvin probe force microscope), MFM (magnetic force microscope), MRFM (magnetic resonance force microscope), NSOM (near-field scanning optical microscope), SNOM (scanning near-field optical microscope), PFM (piezoresponse force microscope), PSTM (photon scanning tunneling microscope), PTMS (photothermal microscope), SECM (scanning electrochemical microscope), SCM (scanning capacitance microscope), SGM (scanning gate microscope), SICM (scanning ion-conductance microscope), SPSM (spin polarized scanning tunneling microscope), SSRM (scanning spreading resistance microscope), SThM (scanning thermal microscope), SVM (scanning voltage microscope), STP (scanning tunneling potentiometry), SHPM (scanning Hall probe microscope), or SXSTM (synchrotron x-ray scanning tunneling microscope), and more desirably AFM or STM.

When a beam is used to remove the said surface described above, it is desirable that the surface is removed using an ion beam or more desirably an atomic ion beam.

Such removal of the surface of the solid-state specimen is to remove the macromolecules, chromosomes, ribosomes or cell organelles that are remaining in the cell after the surface removing sublimation.

One more step can be additionally included to analyze the atomic ratios of the objects to be removed using at least one component to be chosen from a group of electrons, ions, photons and x-ray radiations generated during the removal process by the said ion beams.

The atomic ratios described above can be analyzed using AES (Auger electron spectroscopy), XPS (x-ray photoelectron spectroscopy) or EDX (energy dispersive x-ray spectroscopy).

(d) Acquiring the Surface Information of the Solid-State Specimen

It is desirable to use probes of SPMs (scanning probe microscope) for acquiring the information on the surface of the solid-state specimen. SPMs are instruments for measuring in scales of micrometer or nanometer the physical characteristics of an object to be analyzed. SPMs use probes that are located very close to the surface to be analyzed. The probes can be mounted on cantilevers a few hundred micrometer long and 0.5-5 micrometer thick. SPM methods are disclosed in Wang et al., Amer. Chem. Soc. Lett., 12:1697-98. 1996; Kim et al., Appl. Surface Sci. 130, 230, 340-132:602-609, 1998; Kobayashi et al., Appl. Surface Sci. 157:228-32, 2000; Hirahara et al., Phys. Rev. Lett. 85:5384-87, 2000; Klein et al., Applied Phys. Lett. 78:2396-98, 2001; Huang et al., Science 291:630-33, 2001; Ando et al., Proc. Natl. Acad. Sci. USA 12468-72, 2001.

More desirably, the SPMs used for acquiring the surface information in the present invention are AFM (atomic force microscope), STM (scanning tunneling microscope), BEEM (ballistic electron emission microscope), CFM (chemical force microscope), C-AFM, (conductive atomic force microscope), EFM (electrostatic force microscopy), ESTM (electrochemical scanning tunneling microscope), FMM (force modulation microscope), KPFM (kelvin probe force microscope), MFM (magnetic force microscope), MRFM (magnetic resonance force microscope), NSOM (near-field scanning optical microscope), SNOM (scanning near-field optical microscope), PFM (piezoresponse force microscope), PSTM (photon scanning tunneling microscope), PTMS (photothermal microscope), SECM (scanning electrochemical microscope), SCM (scanning capacitance microscope), SGM (scanning gate microscope), SICM (scanning ion-conductance microscope), SPSM (spin polarized scanning tunneling microscope), SSRM (scanning spreading resistance microscope), SThM (scanning thermal microscope), SVM (scanning voltage microscope), STP (scanning tunneling potentiometry), SHPM (scanning Hall probe microscope), or SXSTM (synchrotron x-ray scanning tunneling microscope), more desirably AFM or STM, and the most desirably AFM.

AFMs are disclosed in U.S. Pat. No. 5,497,656; Moller et al., Biophys. J., 77:1150-8, 1999; Thundat et al., Scanning Microsc. 6:911-8, 1992; Hansma et al., Nucleic Acids Res., 21:505-12, 1993; Murray et al., Proc. Natl. Acad. Sci. USA, 90:3811-4, 1993, and the said documents are inserted in the reference to the present description.

According to an embodiment, the acquisition of the surface information is done by measuring the force between the surface of the solid-state specimen and the probe (desirably Van der Waals force).

The information (for example, three-dimensional images) on the cell surface and the condition inside the cell, the cell surface and the molecules and cell organelles inside the cell can be acquired via the acquisition of the surface information.

According to an embodiment, the present invention additionally includes repeating steps (c) and (d), the three-dimensional images on the cells and viruses to be analyzed can be acquired.

The methods in the present invention can provide the images (desirably, three-dimensional images) on the inside of the cell and the cell membrane surface. In more detail, the methods in the present invention can provide the images on the receptors on the cell surface, channels, cell membrane proteins, cell membrane surface carbohydrates, cell surface markers, cell organelles inside the cells, chromosomes, proteins (for example, enzymes, antibodies, antigens, structural proteins, hormones, growth factors, serum proteins), nucleic acid molecules (for example, DNA, RNA, mRNA, rRNA, tRNA, miRNA, siRNA), carbohydrates and lipids.

other embodiment of the present invention provides an instrument for imaging cells comprising: (a) (i) temperature controller, (ii) pressure controller, or (iii) temperature and pressure controller to maintain at the solid-state a solid-state specimen containing (i) cells, (ii) viruses, (iii) the liquid containing the cells or (iv) the liquid containing the viruses; (b) surface measuring instrument to measure the surface to acquire the surface information of the said solid-state specimen; and (c) Image processor to process the information acquired on the said specimen by the said means to measure the surface and to form images on the said specimen.

The cell imaging apparatus of the present invention is described below in detail.

The application examples of cell imaging using the cell imaging method and the apparatus are explained as below.

Not only the cell surface images but also the information on the various biomolecules existing inside the cells and the molecules constituting the cell organelles, and also the atoms can be acquired using the cell imaging method and the apparatus According to an embodiment. In addition, the information on the interaction among biomolecules and the organic relationship among the cell organelles can be understood. The frozen specimen may contain in reality at least thousands of cells or tens of thousands of cells, and integrating all the information collected from individual cells may yield three-dimensional images of cell components excluding the water in the cells and may confirm the relationship among the cell components.

For example, let us examine a case to examine the influence and effect of an anti-cancer drug on the intracellular mitochondria using the cell imaging method and the apparatus According to an embodiment. First, cultured cells are treated with an anti-cancer drug. The culture media including the cells treated with the anti-cancer drug is rapidly frozen to form a non-crystalline or vitrified ice specimen. The specimen is introduced into the observation chamber (the chamber containing the means to measure the surface), and the surface of the specimen is removed via sublimating the ice by controlling the pressure and temperature of the observation chamber. After the surface of the specimen is removed as much as wanted, the sublimation is suspended by raising the pressure again or by raising the temperature.

As the intracellular mitochondria are the object of interest, the position of the intracellular mitochondria is confirmed using an optical microscope, and the cell surface and other materials are removed to expose the mitochondria to the surface. Afterwards, the surface undulations are observed with surface measuring instrument to acquire the information on the atoms of the specimen surface and their configuration. If necessary, an additional imaging may be done by attaching fluorescent markers, which is a prior art, to the mitochondria or by genetically engineering the mitochondria express fluorescence.

Other embodiment of the present invention provides an analytical method for the objects to be analyzed in the sample comprising the following steps: (a) preparing a solid-state specimen by solidifying the liquid containing the sample; (b) acquiring the surface information of the said solid-state specimen; (c) removing the surface of the said solid-state specimen and to form a new surface; and (d) acquiring the surface information on the new surface of the said solid-state specimen.

Because the method of the present invention is almost identical to the said cell imaging method described above, and because the object of the analysis is the only difference, the common contents of the two will be omitted from the present description in order to avoid too much complexities.

The inventors of the present invention developed the analytical method and the apparatus that can analyze qualitatively and quantitatively the object of analysis with improved sensitivity and accuracy.

In the present description, the definition 'analysis' has meanings to include the judgment on the presence of the object to be analyzed in the specimen (qualitative analysis) and the amount and structure of the object to be analyzed in the specimen (quantitative analysis).

A solid-state specimen of the liquid containing the sample can be prepared at first.

The present invention can be applied to various liquid samples. For example, the samples that the present invention can be applied to include biological samples, chemical samples and environmental samples.

According to an embodiment, the solid-state specimen is prepared by freezing the liquid containing the sample.

The information on the object to be analyzed in the specimen (for example, three-dimensional image) can be acquired, and the presence of the object to be analyzed in the specimen (qualitative analysis) and the amount of the object to be analyzed in the specimen (quantitative analysis) can be determined. Moreover, it can be determined from the said information whether the object to be analyzed combined with other material.

According to a desirable embodiment, the method in the present invention include repeating steps (c) and (d), and the concentration or amount of the said object to be analyzed can be analyzed from the said repetition.

According to an embodiment, after step (d), the method in the present invention can additionally include comparing the information collected from step (d) with the reference surface information from known materials.

The samples used in the present invention can be biological samples. The biological samples that can be used in the present invention include various biological samples, desirably blood, blood plasma, blood serum, lymph, bone marrow, saliva, milk, urine, feces, eye fluid, semen, synovial fluid, thymus fluid, abdominal edema, amniotic fluid, and cell plasma.

The objects to be analyzed in the sample can be proteins (for example, enzymes, receptors, cell membrane proteins, antigens, antibodies, structural proteins, growth factors, hormones, serum proteins, cancer markers) nucleic acid molecules (for example, DNA, RNA, mRNA, rRNA, tRNA, miRNA, siRNA), carbohydrates and small molecular weight compounds.

Also, the objects to be analyzed can be protein-protein compounds interacting each other in the sample. According to an embodiment, the bonding between proteins can be accurately understood.

Also, the objects to be analyzed can be the compounds between drug candidate materials and their target molecules. According to an embodiment, the bonding between drug candidate materials and their target molecules (for example, receptors) can be accurately understood.

Also, the objects to be analyzed can be disease marker materials, more desirably cancer marker materials.

According to the prior art, cancer markers are detected with ELISA (enzyme linked immunosorbent assay), PCR (polymerase chain reaction), and other techniques that utilize antigen-antibody reactions. However, because these detection methods have problems of not only accuracy but also sensitivity, cancer markers in the case of early cancers cannot be detected from biological materials (for example, blood). In the present invention, however, because one single molecule present in a sample can be detected, the cancer markers that cannot be detected by the prior methods, and for these reasons an epochal development can be made in cancer detection.

Other embodiment of the present invention provides an analytical apparatus to analyze the objects to be analyzed comprising: (a) (i) temperature controller, (ii) pressure controller, or (iii) temperature and pressure controller to maintain at the solid-state a solid-state specimen of the liquid containing samples; (b) surface measuring instrument to measure the surface to acquire the surface information of the said solid-state specimen; and (c) image processor to process the information acquired on the said specimen by the said means to measure the surface and to form images on the said specimen.

Other embodiment of the present invention provides an analytical method to analyze the objects in a gas sample to be analyzed, comprising: converting gas samples to liquid samples; solidifying the said liquid sample to prepare a solid-state specimen; acquiring the surface information of the said solid-state specimen; removing the surface of the said solid-state specimen and to form a new surface; acquiring the surface information from the new surface of the said solid-state specimen.

Because the method of the present invention is almost identical to the said cell imaging method, and because the only difference is that the objects to be analyzed are gas samples, the description of the common contents between the two is omitted here.

The information (for example, three dimensional images) on the objects to be analyzed in the gas samples can be acquired by collecting the surface information, and from this, the presence of the objects to be analyzed in the gas sample (qualitative analysis) and the amount of the objects (quantitative analysis) can be determined. The structure of the objects to be analyzed in the samples can be also determined from the said information.

According to an embodiment, repeating steps (c) and (d) can be added, and the concentration or amount of the objects to be analyzed is analyzed.

According to an embodiment, comparing the surface information collected in step (d) and the reference surface information of known materials can be additionally included after step (d).

The objects to be analyzed can be the gases in the atmosphere, viruses, fungi, bacteria, volatile compounds or radiation materials.

The atmosphere can be the atmosphere of streets, hospitals, factories, schools, parks, houses, companies or laboratories or the emission atmosphere of transportation means. Also, the atmosphere can be the expiration of animals.

According to an embodiment, provided is an analytical apparatus for the objects in the gas sample to be analyzed comprising: (a) (i) temperature controller, (ii) pressure controller, or (iii) temperature and pressure controller to maintain the solid-state specimen of the gas sample in the sold state; (b) surface measuring instrument to acquire the surface information of the said solid-state specimen; and (c) Image processor to process the surface information acquired from the said surface measurement means and to form images on the said specimen.

Advantageous Effects

The characteristics and advantages of the present invention is summarized as follows:

(a) The present invention is the cell imaging method to provide information to grasp practically the condition of the cell.

(b) The present invention can provide information on the molecules and atoms consisting various biomolecules and organelles present in the cells.

(c) According to the present invention, the information on the interaction between the biomolecules present in the cells and the organic relationship among intracellular organelles.

BEST MODE

Below, the present invention is described in detail by referencing the attached figures with a desirable exemplary embodiment of the present invention. First, to give reference signs to the components of each figure, it should be noted that the same components are given the same signs even though they are displayed in other figures. In addition, to explain the present invention, the detailed description will be omitted if the detailed description on the disclosed composition or functions related would be judged to make the summary of the present invention ambiguous. In addition, although desirable exemplary embodiment of the present invention will be described in detail, the technological ideas may be of course modified and implemented in various ways by the skilled persons in the art.

Figure 1:
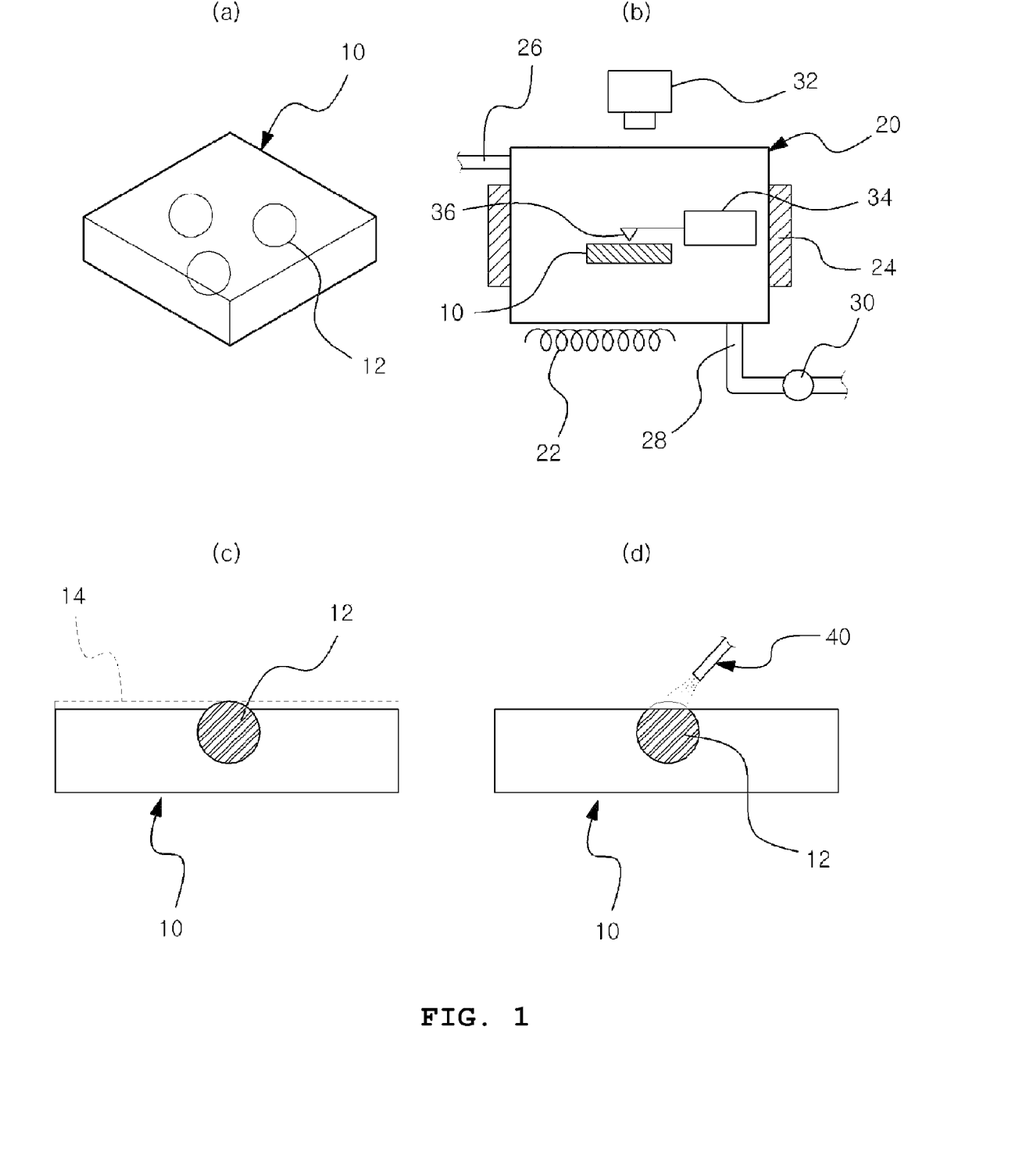
FIG. 1 is a diagram of the cell imaging apparatus and the cell imaging method according to an exemplary detailed embodiment of the present invention.

FIG. 1 is a drawing showing the cell imaging method According to an embodiment.

According to an embodiment, the apparatus includes additionally the solidification means to fabricate a solid-state specimen made by solidifying (i) cells, (ii) viruses, (iii) the liquid containing the cells, (iv) the liquid containing the viruses. More desirably, the said solidification means is the means for freezing.

The cells (12) to be analyzed for the cell imaging According to an embodiment are to be frozen, and more desirably rapidly frozen.

According a desirable exemplary embodiment of the present invention, the freezing means is rapid freezing, and the rapid freezing means transforms the water present inside, outside, or on the surface of cells and viruses into non-crystalline ice.

If it is possible to freeze the cell (12) itself, the cell itself is to be frozen. However, it would be more common to rapidly freeze bodily fluids or culture media containing the cells (12). For example, in the case red blood cells or white blood cells or blood plates are to be imaged, the plasma containing them is to be rapidly frozen. Or the culture media containing the cells are to be rapidly frozen. Frozen specimens (10) are acquired by rapid freezing. In the case liquid-state water is to be rapidly frozen, because crystalline ice is not formed but vitrified ice or non-crystalline ice is formed, damages to the cells (12) do not occur. Accordingly, observations on the real cells in the undamaged state are possible. When bodily fluids or culture media are rapidly frozen, it can be considered that the said bodily fluids or the said culture media may be contained in a tray with the shape of petri dish and frozen rapidly.

The rapidly frozen specimen (10) acquired in FIG. 1 (a) is moved to an observation chamber (20) as shown in FIG. 1 (b). It is desirable that the inside of the observation chamber (20) be maintained below the freezing point to prevent the melting of the specimen (10). In addition, in the case that there exists water vapor in the observation chamber (20), because the water vapor can be frozen on to the inside of the observation chamber (20) or on to the instruments for the imaging, the inside of the observation chamber (20) is desired to be maintained in a state that the water vapor is removed, for example, a nitrogen atmosphere.

An optical microscope (32) may be equipped on the top of the observation chamber (20). The optical microscope (32) performs the function of taking optical images of the specimen (10) containing the cells. In addition, the acquisition of the top surface images of the specimen (10) is possible by equipping an electron microscope instead of an optical microscope. The reason for equipping an optical microscope or an electron microscope is to find the location of the cell or cellular structure to be observed by confirming the image on the specimen (10).

Now that non-crystalline ice is in the solid-state, imaging with molecular or atomic resolutions is possible using atomic force microscopes (AFM) or scanning tunneling microscopes (STM). Therefore, surface measuring instrument (34) to measure the top surface of the specimen and to create images according to the measurements is desirably equipped in the observation chamber. As surface measuring instrument (34), scanning probe microscopes (SPM) that can measure the surface of the specimen with atomic resolutions, and among them, atomic force microscopes (AFM) with different modes can be used. The atomic force microscopes are classified into contact mode and non-contact mode microscopes depending on whether the specimen (10) contacts the probe (36). The information on the specimen surface is acquired by measuring the attractive force (van der Waals force) between the specimen surface and the probe to measure the surface undulation in the case of contact mode, and by measuring the repulsive force in the case of non-contact mode. The contact mode may leave damages to the specimen due to the characteristics of the detection, and as a way to overcome the shortcomings, tapping mode atomic force microscopes (Tapping Mode AFM) may be used. Moreover, surface measuring instrument (34) may be scanning tunneling microscopes.

As shown above, in the case that imaging is done on the specimens including rapidly frozen cells using the surface atomic force microscopes or scanning tunneling microscopes, the minute cell constituents or molecules like the membrane proteins or receptors can be imaged. It is also possible to image cancer markers or other molecules that their amounts in the blood are too low to be detected using prior techniques. It is also possible to measure minute three-dimensional configurations in the case of measuring the specimen surface using atomic force microscopes or scanning tunneling microscopes.

The images acquired in steps above are in reality not three-dimensional images but two-dimensional images of cells. To acquire three-dimensional images, as three-dimensional images are acquired by combining tomographic images, it is necessary to remove the layer whose imaging is finished from the frozen specimen (10) and to acquire the images on the next layers.

As the methods to remove the surface of the frozen specimens, it may be considered to remove the non-crystalline ice on the specimen surface by controlling the temperature and pressure inside the observation chamber (20). In the phase diagram of water, only solid ice and gas-state water vapor exist at the temperatures and pressures below the triple point. Therefore, the solid-state ice sublimes to the gas-state water vapor if, below the triple point, the temperature is raised while maintaining the pressure constant. Or, the solid-state ice sublimes to the gas-state water vapor if, below the triple point, the pressure is lowered while maintaining the pressure constant. Of course, the solid-state ice sublimes to the gas-state water vapor by controlling at below the triple point both the temperature and the pressure. In such ways, the surface of the frozen specimen (10) can be removed by controlling the temperature and the pressure. To control the temperature, heaters (22) and coolers (24) are attached inside the observation chamber (20). To control the pressure, in addition, vacuum pumps (30) connected to the inside of the observation chamber (20) are equipped. On one hand, to remove the gas in the observation chamber (20) including the sublimed water vapor and to supply the gases not containing water vapor, gas exhaust holes (28) are provided in the observation chamber, and gas supply holes (26) are provided to supply gases like nitrogen. As an embodiment, the gas exhaust holes (26) may be connected to the vacuum pumps (30).

FIG. 1 (c) shows the state in which the surface layer of the specimen is removed by a minute thickness using the methods described above. As shown in FIG. 1 (c), after the top surface of the specimen (14) is removed by a minute thickness, images of the cells or the constituent of the cells are acquired using the optical microscopes or surface measuring instrument (34).

Even if the ice included on the specimen surface is removed using the sublimation phenomenon, however, the cell membranes or the various intracellular organelles remain in the specimen without being removed. As the methods to remove them, atomic force microscopes (AFM) or scanning tunneling microscopes (STM) can be directly used to remove by pulling or pushing the cell walls, cell membranes, macro molecules or cellular organelles which were finished with imaging. Or separate probes for removal are equipped in the chamber, and the structures protruded to the specimen top surface may be removed using the removal probes.

According to a desirable exemplary embodiment, the SPMs with probes as surface measurement means are used as the surface removal means to remove the surface of the solid-state specimen with physical forces.

As another method, it may be considered that ion beams may be used to remove the protruded structures. FIG. 1 (d) shows the state that the protruded structures are removed using the ion beams (40).

When ion beams are used, it is additionally possible to analyze the atomic ratios of the removed materials by analyzing the electrons, ions, photons, or x-ray radiations generated while the materials are removed with the ion beams. For this, the atomic analysis part is equipped in the observation chamber (20).

According to an embodiment, the apparatus of the present invention includes additionally spectroscopes to acquire the chemical composition of the frozen specimen, more desirably AES (Auger electron spectroscope), XPS (x-ray photoelectron spectroscope) or EDX (energy dispersive x-ray spectroscope).

Figure 2:
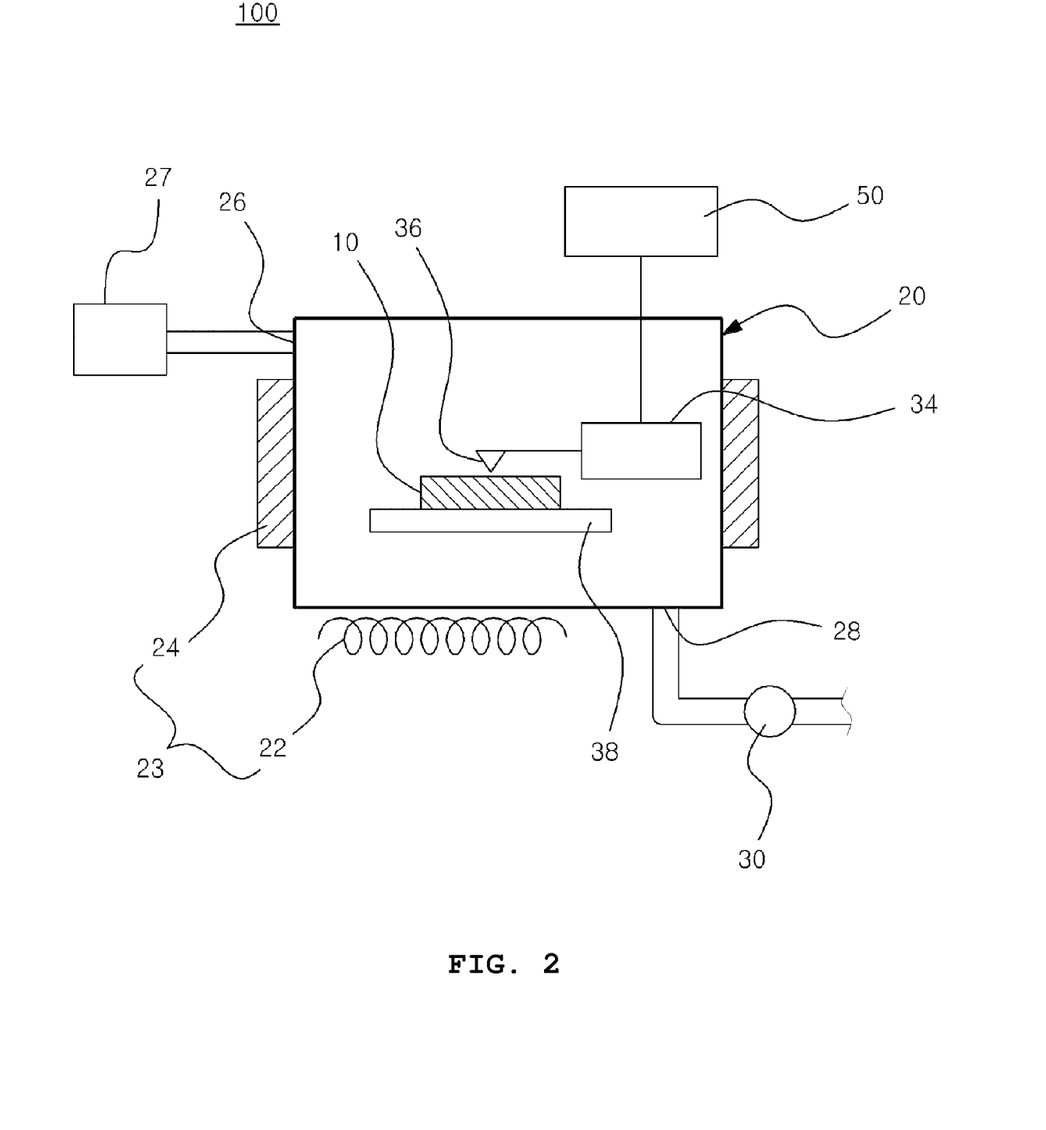
FIG. 2 is a diagram of the cell imaging apparatus according to an exemplary detailed embodiment of the present invention.

FIG. 2 is a drawing showing the construction of the cell imaging apparatus according to a desirable exemplary embodiment.

The cell imaging apparatus in the present invention includes (a) (i) the temperature controller, (ii) the pressure controller, or (iii) the temperature and pressure controller; (b) surface measuring instrument to acquire the surface information of the said sold-state specimen; and (c) image processor to process the surface information acquired from the said surface measurement means and to form the images on the said specimen.

The said temperature/pressure controller and surface measuring instrument may be laid out in various ways. For example, the temperature controller and/or the pressure controller and surface measuring instrument may be located in one chamber. Moreover, the temperature controller and/or the pressure controller and surface measuring instrument may be located in one chamber separately from the said solidification means (for example, the freezing means), or the solidification means, the temperature controller and/or the pressure controller and surface measuring instrument may be located in separate chambers.

It may be the most desirable that the temperature controller and/or the pressure controller and surface measuring instrument be located in a chamber that is separate from the chamber that houses the solidification means (for example, the freezing means). The chamber with surface measuring instrument is called the observation chamber.

The observation chamber (20) houses the rapidly frozen cells or the frozen specimens of bodily fluid or culture media. In order to maintain the atmosphere dehumidified, such an observation chamber is equipped with a dehumidified gas supply part (27) and a gas supply part (26) located at one side to supply the dehumidified air or to maintain the atmosphere with nitrogen gas. In addition, the gas exhaust hole (28) to pump the gas to the outside is equipped at one side of the chamber (20), for example, at the bottom of the observation chamber (20). A specimen table to position the frozen specimen (10) may be equipped at the center of the chamber (20).

On one hand, the temperature controller (23) to control the temperature is provided in the observation chamber (20), and the temperature controller (23) together with the cooler part (24) and the heater part (22) can increase or decrease the temperature inside the chamber (20). The chamber (20) is connected with the pressure controller (30) to control the pressure of the chamber (20). In an exemplary embodiment, the said pressure controller may be constituted of vacuum pumps.

By such construction, with a frozen specimen (10) positioned inside the observation chamber, the frozen specimen can be prevented from melting. On one hand, the top ice on the frozen specimen (10) can be removed by sublimation by controlling the temperature or the pressure with the temperature and pressure in the chamber (20) with the temperature and the pressure maintained below the triple point. The gases including the sublimated water vapor inside the observation chamber (20) is pumped out through the gas exhaust hole (28), dehumidified gas is again supplied into the observation chamber (20) through the gas supply hole (26). Surface measuring instrument is provided in the observation chamber (20), and surface measuring instrument may be atomic force microscopes or scanning tunneling microscopes. The probes of the atomic force microscopes or the scanning tunneling microscopes are positioned inside the chamber (20) and measure the top surface of the frozen specimen. On one hand, besides that the said probes measure the top surface of the frozen specimen, the said probes can be also used as to remove the cellular structures on the top of the frozen specimen.

Image processor (50) processes the surface information of the frozen specimen (10) measured by the probes (26) of surface measuring instrument (34) and forms two-dimensional images. Desirably, the image processing part (50) is connected to the visual display apparatus (not displayed) and displays the two-dimensional images processed. On one hand, the information acquired by surface measuring instrument (34) may be the three-dimensional images with minute depths.

As described in detail above, the images on the new layers can be acquired by sublimating the top ice of the frozen specimen or by removing the cellular structure. Image processor (50) may assemble the images of multi layers acquired by repeating the procedure and form the three-dimensional images on the cells or the elements constituting the cells.

As such the specific parts of the present invention has been described in detail, these specific technologies are only desirable exemplary embodiment, and the scopes of the present invention are apparently not to be restricted. Therefore, the practical scopes of the present invention are defined by the attached claims and their equivalents.

Description of Reference Symbol

| | |
|---|---|
| 10: frozen specimen (solid-state specimen) | 12: cell |
| 14: surface of the frozen specimen | 20: observation chamber |
| 22: heater | 23: temperature controller |
| 24: cooler part | 26: gas supply hole |
| 27: gas supply part | 28: gas exhaust hole |
| 30: vacuum pump (pressure controller) | 32: microscope |
| 34: surface measurement means | 36: probe |
| 38: specimen table | 40: ion beam |
| 50: image processing means | 100: apparatus for cell imaging |

As such the specific parts of the present invention have been described in detail, these specific technologies are only desirable exemplary embodiment, and the scopes of the present invention are apparently not to be restricted. Therefore, the practical scopes of the present invention are defined by the attached claims and their equivalents.

What is claimed is:

1. A method for obtaining an atomic resolution image of solute in solvent, comprising:
   (a) preparing a solid-phase specimen by solidifying the solvent, in order to fix a position of the solute in the solvent;
   (b) acquiring surface information on the solid-phase specimen by a scanning probe microscope;
   (c) removing a surface of the solid-phase specimen by sublimation for the solvent and then by physical forces or energetic beams for the solute, in order to form a new surface; and
   (d) acquiring the surface information on the new surface of the solid-phase specimen by the scanning probe microscope.

2. The method of claim 1, wherein said solidifying is implemented by rapid solidification.

3. The method of claim 2, wherein said rapid solidification is accomplished such that a non-crystalline phase of the solvent is formed so as not to damage the solute.

4. The method of claim 1, wherein said sublimation is implemented by controlling a pressure at a constant temperature below the triple point.

5. The method of claim 1, wherein said sublimation is implemented by controlling a temperature at a constant pressure below the triple point.

6. The method of claim 1, further including
   analyzing an atomic composition of the solute to be removed by at least one selected from a group consisting of electrons, ions, photons, and x-ray beams.

7. The method of claim 1, wherein repeating steps (c) and (d) is further included such that a three dimensional image of the solute is acquired by said repeating steps.

8. An apparatus for obtaining an atomic resolution image of solute in solvent, comprising:
   (a) a temperature or a pressure controller to maintain a solid-phase specimen fabricated by solidifying the solvent at a solid phase;
   (b) a surface measuring instrument to acquire surface information on the solid-phase specimen by a scanning probe microscope (SPM);
   (c) a surface removal instrument to remove a surface of the solid-phase specimen by sublimation for the solvent and then by physical forces or energetic beams for the solute, in order to form a new surface; and
   (d) an image processor to process the surface information acquired from the surface measuring instrument and to form the atomic resolution image on the solid-phase specimen.

9. The apparatus of claim 8, wherein the said apparatus further includes a solidification instrument to fabricate the solid-phase specimens by solidifying the solvent, in order to fix a position of the solute in the solvent.

10. The apparatus of the claim 8, wherein the apparatus further includes an optical microscope or an electron microscope.

11. The apparatus of the claim 8, the SPM equipped with a probe as the surface measuring instrument is used as the surface removal instrument to remove the surface of the solid-phase specimen by the physical forces.

* * * * *